(12) United States Patent
Yun et al.

(10) Patent No.: US 10,153,141 B2
(45) Date of Patent: Dec. 11, 2018

(54) APPARATUS FOR MONITORING GAS AND PLASMA PROCESS EQUIPMENT INCLUDING THE SAME

(71) Applicant: Electronics and Telecommunications Research Institute, Daejeon (KR)

(72) Inventors: Sun Jin Yun, Daejeon (KR); Kyu Sung Lee, Seoul (KR); JungWook Lim, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 0 days.

(21) Appl. No.: 14/621,739

(22) Filed: Feb. 13, 2015

(65) Prior Publication Data

US 2015/0235816 A1 Aug. 20, 2015

(30) Foreign Application Priority Data

Feb. 14, 2014 (KR) .................. 10-2014-0017207
Aug. 29, 2014 (KR) .................. 10-2014-0113902

(51) Int. Cl.
*H01J 37/32* (2006.01)
*G01N 33/00* (2006.01)
*G01N 21/64* (2006.01)

(52) U.S. Cl.
CPC .... *H01J 37/32963* (2013.01); *G01N 33/0027* (2013.01); *H01J 37/32834* (2013.01); *H01J 37/32981* (2013.01); *G01N 2021/6417* (2013.01)

(58) Field of Classification Search
CPC .......... H01J 37/32963; H01J 37/32981; H01J 37/3244; H01J 37/32834; G01N 21/64; G01N 33/0027; G01N 21/6402; G01N 2201/06113; G01N 2201/068; G01N 2021/6417
See application file for complete search history.

(56) References Cited

U.S. PATENT DOCUMENTS

| 4,637,938 A | 1/1987 | Lee et al. |
| 4,675,072 A | 6/1987 | Bennett et al. |
| 5,748,319 A | 5/1998 | Baek et al. |

(Continued)

FOREIGN PATENT DOCUMENTS

| JP | 2000310697 A | * 11/2000 |
| KR | 20070048210 A | 5/2007 |

(Continued)

*Primary Examiner* — Yuechuan Yu
(74) *Attorney, Agent, or Firm* — Rabin & Berdo, P.C.

(57) ABSTRACT

Provided is an apparatus for monitoring a gas and plasma process equipment including the same. The apparatus includes: a housing including a gas inflow hole, a gas discharge hole, and windows; a light source disposed adjacent to one of the windows outside the housing to provide source light to a gas supplied between the gas inflow hole and the gas discharge hole; a sensor disposed adjacent to the other of the windows outside the housing to detect fluorescence emitted from the gas by the source light; and a coil disposed in the housing between the gas inflow hole and the gas discharge hole to heat and decompose the gas between the light source and the sensor, thereby increasing the fluorescence emitted from the gas.

19 Claims, 7 Drawing Sheets

(56) References Cited

U.S. PATENT DOCUMENTS

| | | | |
|---|---|---|---|
| 5,966,586 A * | 10/1999 | Hao | H01J 37/32963 |
| | | | 438/14 |
| 6,334,928 B1 * | 1/2002 | Sekine | B01D 8/00 |
| | | | 118/61 |
| 6,686,594 B2 | 2/2004 | Ji et al. | |
| 2002/0073922 A1 * | 6/2002 | Frankel | C23C 16/401 |
| | | | 118/715 |
| 2002/0093652 A1 * | 7/2002 | Powell | G01N 21/68 |
| | | | 356/316 |
| 2006/0021633 A1 | 2/2006 | Harvey | |
| 2006/0042544 A1 * | 3/2006 | Hasebe | C23C 16/4405 |
| | | | 118/715 |
| 2008/0257014 A1 | 10/2008 | Yamamoto et al. | |
| 2009/0041925 A1 | 2/2009 | Lewis et al. | |
| 2009/0263919 A1 * | 10/2009 | Hori | C23C 8/10 |
| | | | 438/5 |
| 2009/0288684 A1 * | 11/2009 | Kitaoka | C23C 16/4407 |
| | | | 134/21 |
| 2012/0273005 A1 | 11/2012 | Ramachandran et al. | |

FOREIGN PATENT DOCUMENTS

| | | |
|---|---|---|
| KR | 10-2008-0093926 A | 10/2008 |
| KR | 20-2011-0002066 U | 3/2011 |
| WO | WO-01/027596 A1 | 4/2001 |

* cited by examiner

APPARATUS FOR MONITORING GAS AND PLASMA PROCESS EQUIPMENT INCLUDING THE SAME

CROSS-REFERENCE TO RELATED APPLICATIONS

This U.S. non-provisional patent application claims priority under 35 U.S.C. § 119 to Korean Patent Application Nos. 10-2014-0017207, filed on Feb. 14, 2014, and 10-2014-0113902, filed on Aug. 29, 2014, the entire contents of which are hereby incorporated by reference.

BACKGROUND OF THE INVENTION

The present invention disclosed herein relates to an apparatus for monitoring a process, and more particularly, to an apparatus for monitoring a gas, which detects fluorescence of an exhausted product gas and plasma process equipment including the same.

In general, silicon and silicon compounds are the most important material in solar cell and semiconductor fields. The silicon and silicon compounds are used for various purposes such as the formation of a semiconductor thin film, an insulator film, a protective film, and a buffer layer. A silicon thin film and silicon compound thin film may be formed on a substrate by mainly using vacuum deposition equipment. The vacuum deposition equipment may be polluted and unintentional deposits may be accumulated on the wall in proportion to usage time. Accordingly, the vacuum deposition equipment requires time-consuming dry-cleaning process every predetermined cumulative time.

A dry cleaning is a method of cleaning the inside of a chamber of the vacuum deposition equipment through plasma reaction. For example, a dry cleaning process gas of a chamber in which a thin film such as Si, $SiO_2$, $Si_3N_4$, and SiC is deposited may include fluoride compounds such as $SF_6$, $CF_4$, $C_2F_6$, and $NF_3$ which have excellent etching characteristics. However, since the fluoride compounds are greenhouse gases accelerating global warming, their emission has to be restricted. In addition, since the fluoride compounds are relatively expensive, cleaning costs may increase when a large amount of cleaning gas is used.

A method of measuring a cleaning endpoint may efficiently prevent or reduce economic and environmental losses by reducing excess consumption of cleaning gases. The cleaning endpoint of the dry cleaning process may be measured by a surface reflectance of a solid specimen, an etch stop layer, or an optical emission spectroscopy (OES). The OES may provide information concerning the cleaning endpoint through a spectrum change of species in plasma during cleaning process. In recent years, plasma process equipment that monitors the behavior of light emitted from a species in plasma to detect the cleaning endpoint has been suggested. However, an endpoint detection error may occur by interference in the plasma reaction. Furthermore, OES spectra are highly complicated, and thus expensive equipment such as a monochromater is required for exactly measuring a pattern for each wavelength to detect the endpoint.

SUMMARY OF THE INVENTION

The present invention provides an apparatus for monitoring a gas, which detects fluorescence having no interference in plasma reaction within a chamber, and plasma process equipment including the same.

Embodiments of the present invention provide apparatuses for monitoring a gas include a housing including a gas inflow hole, a gas discharge hole, and windows; a light source disposed adjacent to one of the windows outside the housing to provide source light to a gas supplied between the gas inflow hole and the gas discharge hole; a sensor disposed adjacent to the other of the windows outside the housing to detect fluorescence emitted from the gas by the source light; and a coil disposed in the housing between the gas inflow hole and the gas discharge hole to heat and decompose the gas between the light source and the sensor, thereby increasing the fluorescence emitted from the gas.

In some embodiments, the coil may include a filament.

In other embodiments of the present invention, plasma process equipment includes: a chamber in which a plasma process is performed; a pumping tube for exhausting a gas in the chamber; and a gas monitoring apparatus for detecting an endpoint of the plasma process from the reaction gas in the pumping tube, wherein the gas monitoring apparatus includes: a housing comprising a gas inflow hole, gas discharge hole, and windows; a light source disposed adjacent to one of the windows outside the housing to provide source light to a gas supplied between the gas inflow hole and the gas discharge hole; a sensor disposed adjacent to the other of the windows outside the housing to detect the fluorescence emitted from the gas by the source light; and a coil disposed in the housing between the gas inflow hole and the gas discharge hole to heat and decompose the gas between the light source and the sensor, thereby increasing the fluorescence emitted from the gas.

BRIEF DESCRIPTION OF THE DRAWINGS

The accompanying drawings are included to provide a further understanding of the present invention, and are incorporated in and constitute a part of this specification. The drawings illustrate exemplary embodiments of the present invention and, together with the description, serve to explain principles of the present invention. In the drawings.

DETAILED DESCRIPTION OF PREFERRED EMBODIMENTS

Figure 1:
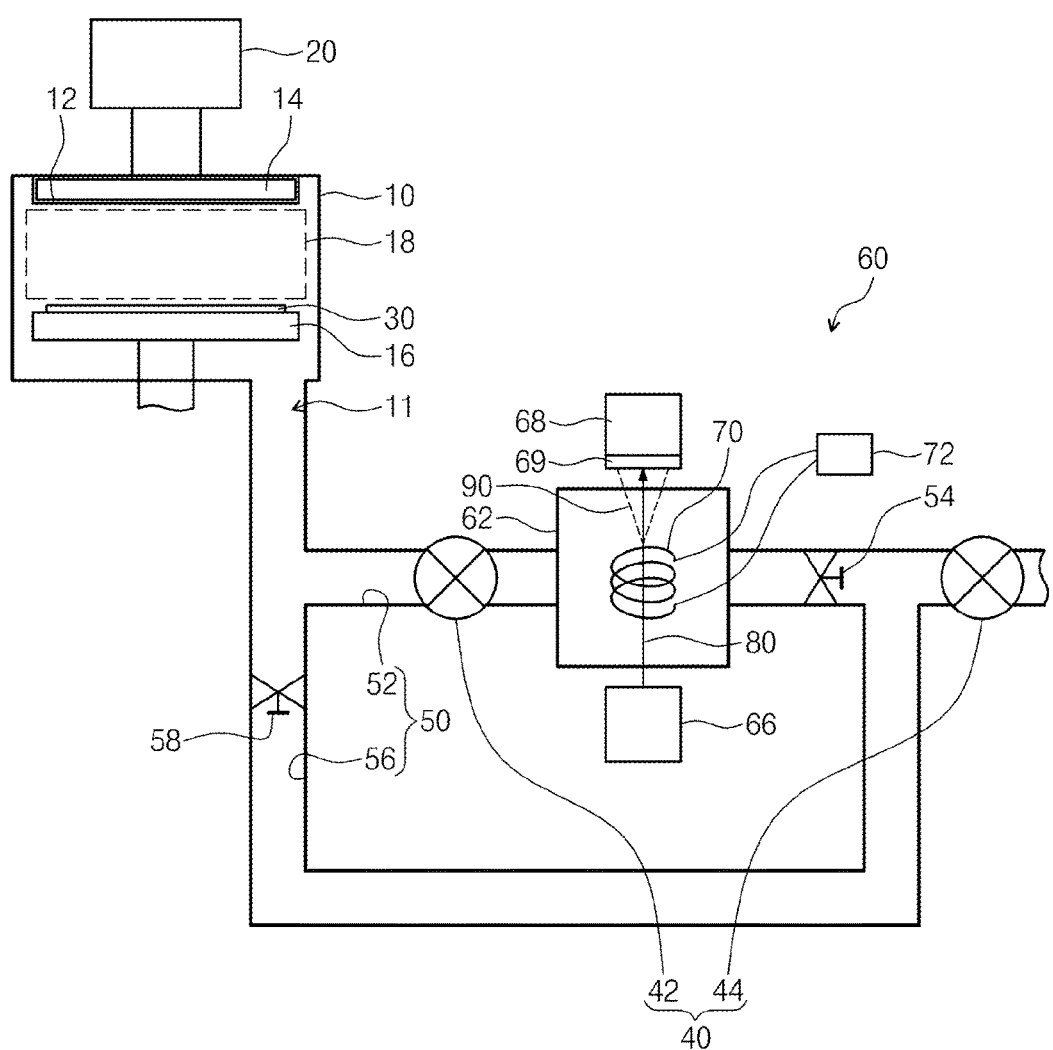
FIG. 1 is a schematic view illustrating plasma process equipment according to an embodiment of the present invention.

Hereinafter, exemplary embodiments of the present invention will be described in detail with reference to the accompanying drawings. Advantages and features of the present invention, and implementation methods thereof will be clarified through following embodiments described with reference to the accompanying drawings. The invention may, however, be embodied in many different forms and should not be construed as being limited to the embodiments set forth herein. Rather, these embodiments are provided so that this disclosure will be thorough and complete, and will fully convey the scope of the present invention to those skilled in the art. Further, the present invention is only defined by scopes of claims. Like reference numerals refer to like elements throughout.

In the following description, the technical terms are used only for explaining a specific exemplary embodiment while not limiting the present invention. The terms of a singular form may include plural forms unless referred to the contrary. The meaning of "include," "comprise," "including," or "comprising," specifies a property, a region, a fixed number, a step, a process, an element and/or a component but does not exclude other properties, regions, fixed numbers, steps, processes, elements and/or components. Also, laser pulse and laser beam used in the specification represent the same light, and terms including spectrum, pulse width, parallel beam and beam size may be understood as general optical terms relating to wavelength, intensity, and dose of laser pulse. Since preferred embodiments are provided below, the order of the reference numerals given in the description is not limited thereto.

FIG. 1 is a schematic view illustrating plasma process equipment 100 according to an embodiment of the present invention. The plasma process equipment 100 may include a process chamber 10, a reaction gas supply unit 20, vacuum pumps 40, pumping tubes 50, and a gas monitoring apparatus 60.

The process chamber 10 may provide a reaction gas for plasma reaction 18 onto a substrate 30. A shower head 12, a high frequency electrode 14, and a chuck 16 may be disposed in the process chamber 10. The shower head 12 may spray the reaction gas onto the substrate 30. The high frequency electrode 14 may supply a high frequency electrical power to the reaction gas in the process chamber 10 to induce the plasma reaction. The chuck 16 may fix and cool down the substrate 30 with respect to the reaction gas.

The reaction gas supply unit 20 may supply the reaction gas, for example, a deposition gas and a cleaning gas into the process chamber 10. The deposition gas is a source gas for forming silicon or silicon-compound films on the substrate 30. For example, the deposition gas may include silane ($SiH_4$), germane ($GeH_4$), ammonia ($NH_3$), oxygen ($O_2$), or hydrogen ($H_2$). The deposition gas may generate the silicon or the silicon compound on the substrate 30 through the plasma reaction 18. On the contrary, the deposition gas may generate unintentional deposits of silicon or silicon compound on an inner wall of the process chamber 10. The cleaning gas cleans the substrate 30 or the inside of the process chamber 10. The cleaning gas may include sulphur hexafluoride ($SF_6$), carbon fluoride ($CF_4$, $C_2F_6$), nitrogen fluoride ($NF_3$) or any other F-containing gases. The cleaning gas may remove the unintentional deposits (pollutants) of silicon or silicon compound on the inner wall of the chamber through the plasma reaction 18.

The vacuum pumps 40 connected to the pumping tube 52 through valves may pump the process chamber 10. According to an example, the vacuum pumps 40 may include a first vacuum pump 42 and a second vacuum pump 44. The first vacuum pump 42 is a high vacuum pump that pumps the reaction gas at high vacuum of about $10^{-5}$ Torr or less. For example, the first vacuum pump 42 may include a turbo pump, an ion pump, or a cryo-pump. The second vacuum pump 44 is a low vacuum pump that pumps the reaction gas at low vacuum of about $10^{-3}$ Torr or less. The second vacuum pump 44 may include a dry pump or a rotary pump.

Pumping tubes 50 may connect the process chamber 10 to vacuum pumps 40. The pumping tubes 50 may include a main pumping tube 52 and a roughing tube 56. The main pumping tube 52 may connect the first vacuum pump 42 to the second vacuum pump 44 in series. The first vacuum pump 42 and the second vacuum pump 44 may be disposed on the main pumping tube 52. On the other hand, the process chamber 10 and the main pumping tube 52 may be connected to each other through the first vacuum pump 42. The first vacuum pump 42 may be connected to an exhaust port 11 of the process chamber 10. A main valve 54 may be disposed on the main pumping tube 52 between the first vacuum pump 42 and the second vacuum pump 44. The roughing tube 56 may detour the first vacuum pump 42 and the main valve 54. For example, the roughing tube 56 may be branched from the main pumping tube 52 disposed on a front end of the first vacuum pump 42 and reconnected to the main pumping tube 52 disposed on a rear end of the first vacuum pump 42. A roughing valve 58 may be disposed on the roughing tube 56. The main valve 54 and the roughing valve 58 may be opened/closed alternately and/or exclusively. When the process chamber 10 is initially pumped, the main valve 54 is closed, and the roughing valve 58 is opened. When the main valve 54 is opened, and the roughing valve 58 is closed, the plasma reaction of the reaction gas in the process chamber 10 may be induced. When the plasma reaction is finished, the main valve 54 and the roughing valve 58 may be opened/closed alternately. The deposition gas or cleaning gas may be concentrated onto the substrate 30 during the plasma reaction when a thin film deposition process or an etching process is performed on the substrate 30. During cleaning process, the cleaning gas may etch the unintentional deposits on substrate holders, electrodes, and other parts in the plasma chamber.

The gas monitoring apparatus 60 may monitor a kind of exhaust gas that is exhausted through the pumping tubes 50. According to an example, the gas monitoring apparatus 60 may be disposed on the main pumping tube 52 between the first vacuum pump 42 and the second vacuum pump 44. Also, the gas monitoring apparatus 60 may be coupled to the main pumping tube 52 between the first vacuum pump 42 and the main valve 54. The exhaust gas may include an exhausted product gas and a reactive exhaust gas. The exhausted product gas is generated after the deposition process or the cleaning process is completed and has relatively high stability in comparison to the reactive exhaust gas. The exhausted product gas may include a silicon fluoride (Si—F) compound. The reactive exhaust gas is an exhaust gas that is not involved in the deposition process or the cleaning process. The reactive exhaust gas may have high reactivity and be unstable. A discharge amount of reactive exhaust gas has to be minimized. Since a high frequency power is not supplied to the exhausted product gas and the reactive exhaust gas in the pumping tubes 50, they may not emit light by themselves. The gas monitoring apparatus 60 may supply source light 80 to the exhaust gas. The gas monitoring apparatus 60 may detect fluorescence 90 generated from activated Si—F species originated from the exhausted product gas by the source light 80. When the gas monitoring apparatus 60 detects the fluorescence 90, it is not necessary to consider about the interference by the plasma reaction 18. The gas monitoring apparatus 60 may monitor a change in fluorescence to provide information with respect to the variation in amount of the product gas in the pumping tubes 50. Accordingly, the gas monitoring apparatus 60 may provide information with respect to a processing endpoint of the plasma process.

Figure 2:
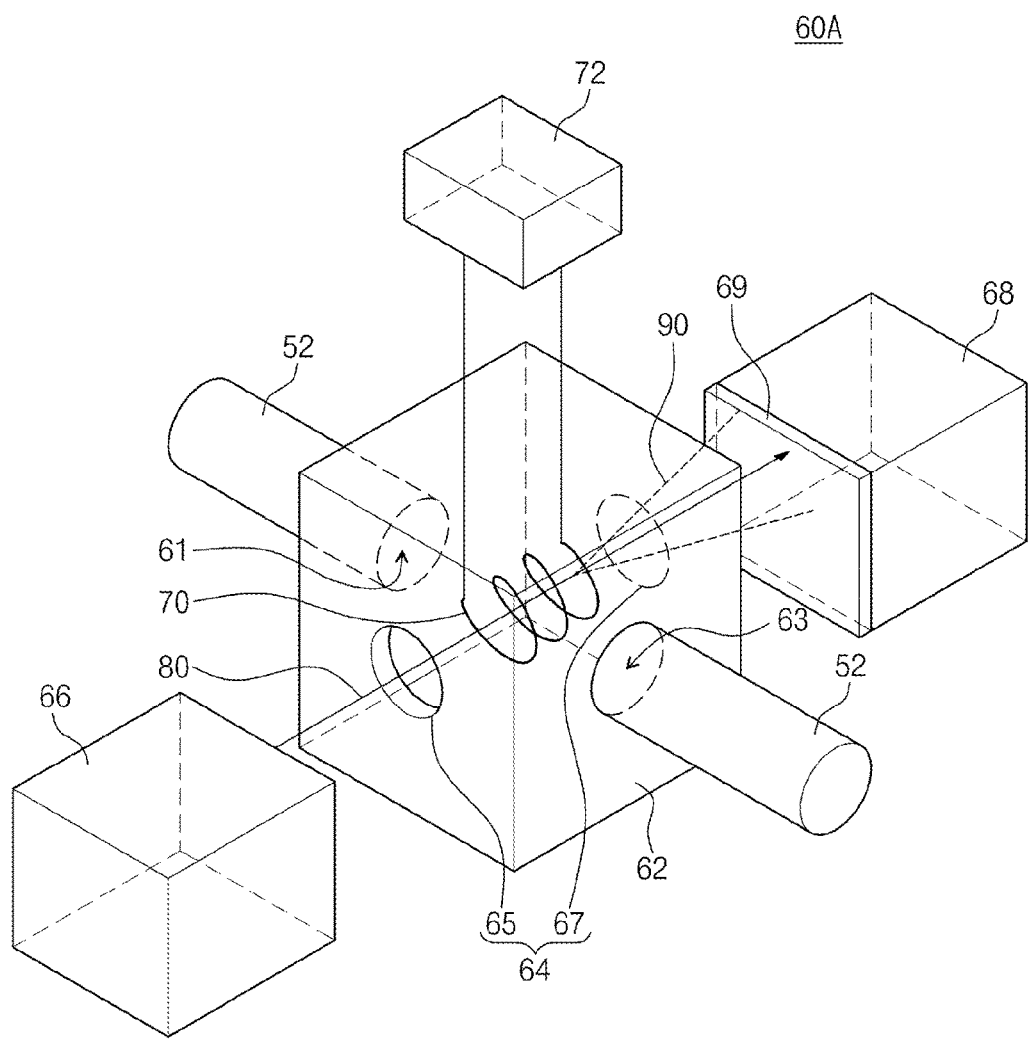
FIG. 2 is a perspective view of a gas monitoring apparatus in FIG. 1.

FIG. 2 is a perspective view illustrating an example 60A of the gas monitoring apparatus of FIG. 1. The gas monitoring apparatus 60A may include a housing 62, a light source 66, a first sensor 68, an optical filter 69, a coil 70, and a power supply unit 72.

The housing 62 may be connected to the main pumping tube 52. The housing 62 may include a gas inflow hole 61, a gas discharge hole 63, and windows 64. The gas inflow hole 61 and the gas discharge hole 63 may be defined in both walls, facing each other, of the housing 62. The gas inflow hole 61 may be adjacent to the first vacuum pump 42. The gas discharge hole 63 may be adjacent to the second vacuum pump 44 and the main valve 54. The windows 64 may include a first window 65 and a second window 67. The first window 65 and the second window 67 may be disposed in a direction different from that of the gas inflow hole 61 and the gas discharge hole 63.

The light source 66 may be disposed outside the first window 65 of the housing 62. The light source 66 may supply a source light 80 into the housing 62. The source light 80 may be irradiated to the exhausted product gas of cleaning process. For example, the source light 80 may include a blue laser or ultraviolet laser beam, and the light source 66 may include a laser. For example, the exhausted product gas of the silicon fluoride compound may emit blue fluorescence 90 having a wavelength longer than that of the light source from the ultraviolet laser beam or the blue light.

Figure 3:
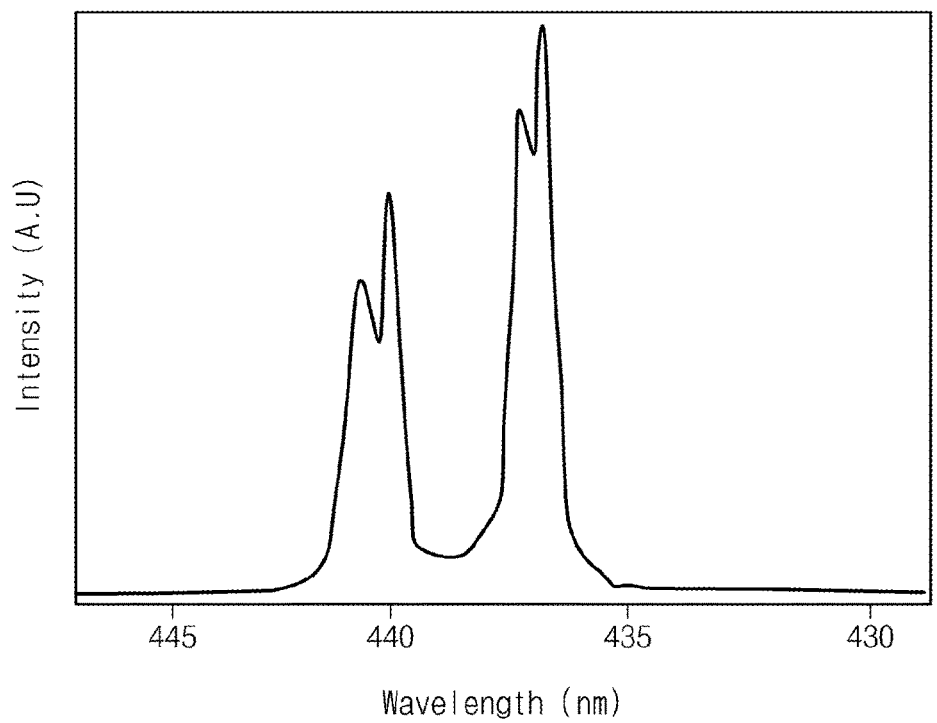
FIG. 3 is a graph showing intensity according to a wavelength of fluorescence of a silicon fluoride compound.

FIG. 3 is a graph showing intensity according to a wavelength of fluorescence of a silicon fluoride compound. Fluorescence 90 of the exhausted product gas of the silicon fluoride compound may have peaks of intensity at wavelengths of about 440 nm and about 437 nm.

Referring again to FIG. 2, a first sensor 68 may be disposed outside the second window 67 of the housing 62. The first sensor 68 may detect the fluorescence 90 of the exhausted product gas. The fluorescence 90 may have a wavelength longer than that of the source light 80 of the laser beam which is the light source. The first sensor 68 may include a CMOS or CCD.

An optical filter 69 may be disposed between the first sensor 68 and the second window 67. The optical filter 69 may remove the source light 80. For example, the optical filter 69 may include transparent glass and transparent plastic. The first sensor 68 may detect the fluorescence from which the source light 80 is removed.

A coil 70 may be disposed in the housing between the light source 66 and the first sensor 68. According to an example, the coil 70 may include a filament. The coil 70 may be wounded along a direction in which the light source 66 and the first sensor 68 are arranged. That is, the coil 70 may have a circular shape aligned in the direction in which the light source 66 and the first sensor 68 are arranged. The coil 70 may be aligned in a direction crossing a direction in which the gas inflow hole 61 and the gas discharge hole 63 are arranged. The fluorescence 90 may radially progress with respect to the second window 67 along the coil. The hot coil may decompose the exhausted product gas into Si—F species emitting fluorescence when the source light is absorbed.

The power supply unit 72 may provide an electric power to the coil 70. The coil 70 may be heated in proportion to the electric power. For example, the coil 70 may heat the exhausted product gas at a temperature of about 1000 or higher to activate and decompose the exhausted product gas.

When the source light 80 is irradiated onto the activated and decomposed exhaust gas, the exhausted product gas may emit fluorescence.

The plasma process equipment 100 may determine a cleaning endpoint in the process chamber 10 through a variation in fluorescence 90.

Figure 4:
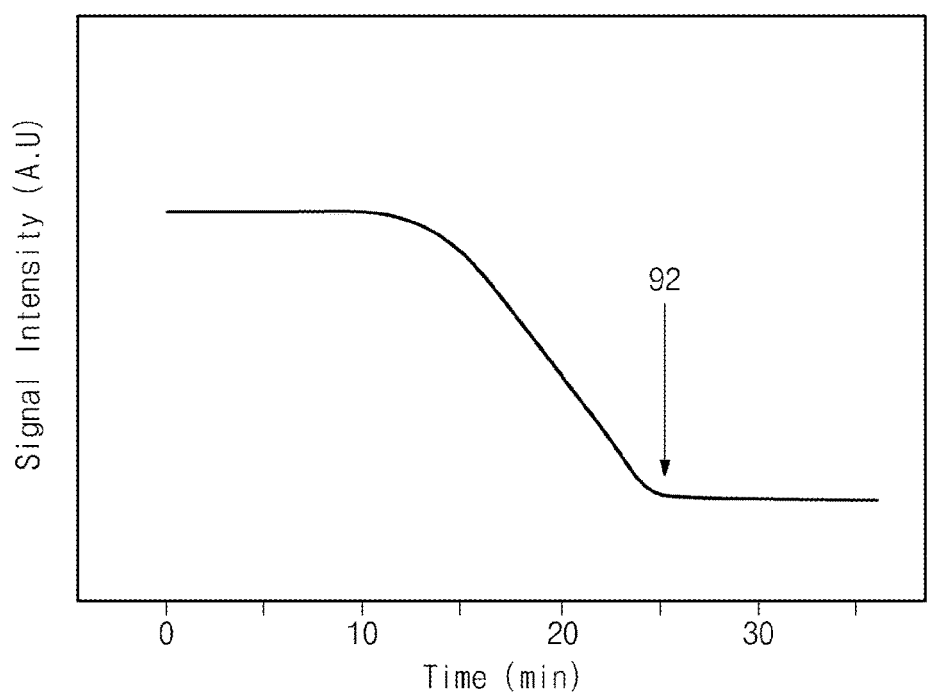
FIG. 4 is a graph showing a cleaning endpoint.

FIG. 4 is a graph showing a cleaning endpoint 92. When the fluorescence 90 is reduced in signal intensity till the cleaning endpoint 92, the plasma process equipment 100 may complete the cleaning process in the process chamber 10. The cleaning endpoint 92 is a criterion representing the completion of the cleaning process in the process chamber 10. For example, the silicon fluoride may be reduced during the cleaning process of the process chamber 10. When the fluorescence 90 of the silicon fluoride is not practically detected or minimized, the cleaning process of the process chamber 10 may be finished.

Figure 5:
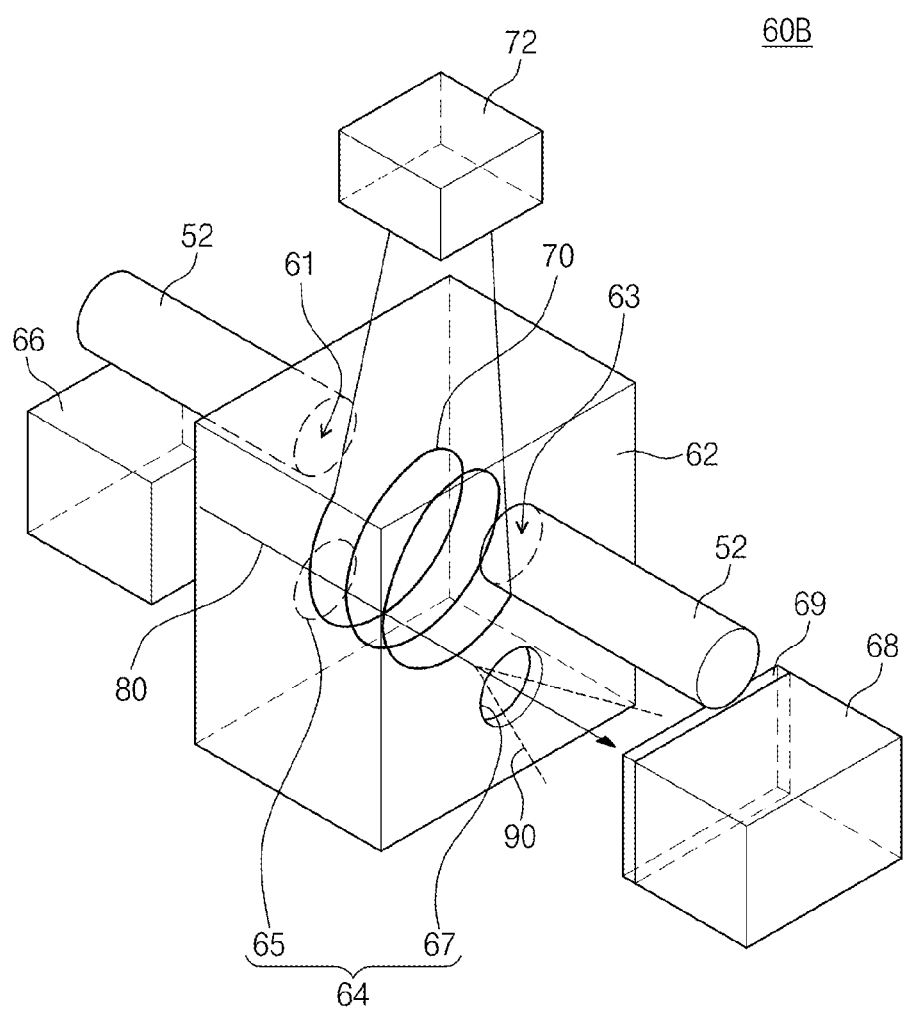
FIG. 5 is a perspective view of a gas monitoring apparatus according to an exemplary embodiment of the present invention.

FIG. 5 is a perspective view of a gas monitoring apparatus 60B according to an exemplary embodiment of the present invention. The first window 65 and the second window 67 of the housing 62 may be arranged in a direction in which the gas inflow hole 61 and the gas discharge hole 63 are arranged. For example, the first window 65 and the second window 67 may be disposed below the gas inflow hole 61 and the gas discharge hole 63, respectively. The main pumping tube 52 connected to the gas inflow hole 61 and the gas discharge hole 63 may be disposed on the light source 66 and the first sensor 68

The source light 80 may be supplied into the housing 62 and the coil 70 through the first window 65. According to an example, the coil 70 may be aligned along the first window 65 and the second window 67. Accordingly, the coil 70 may be aligned in the direction in which the gas inflow hole 61 and the gas discharge hole 63 are arranged.

Figure 6:
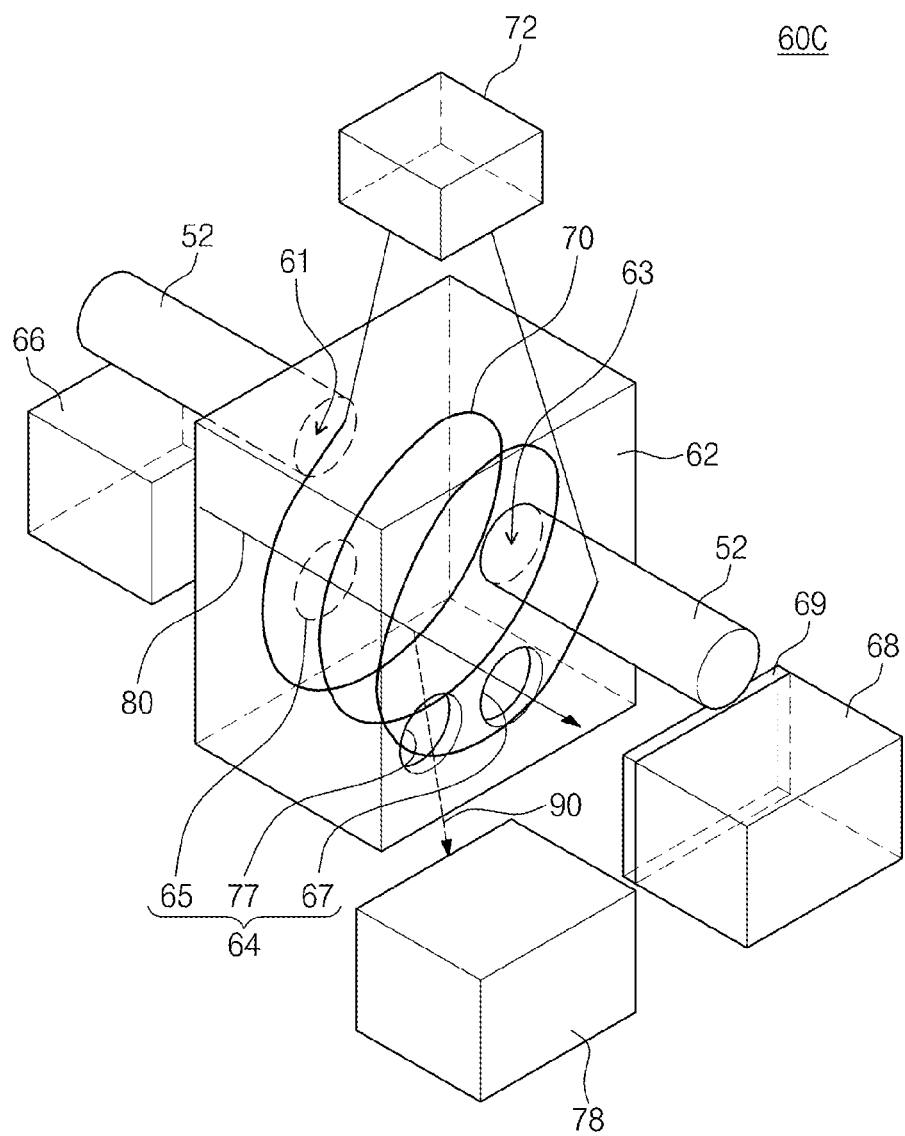
FIG. 6 is a perspective view of a gas monitoring apparatus according to another exemplary embodiment of the present invention.

FIG. 6 is a perspective view of a gas monitoring apparatus 60B according to another exemplary embodiment of the present invention. The gas monitoring apparatus 60C may include a second sensor 78 disposed outside a third window 77 of the housing 62.

The third window 77 may be adjacent to the second window 67. The source light 80 with excellent straightness may be supplied to the first window 65 and the second window 67 of windows 64. The source light 80 passes through the first window 65 and the second window 67. The source light 80 may not be supplied to the third window 77 among the windows 64. The fluorescence 90 may progress diagonally with respect to an alignment direction of the first window 65 and the second window 67. The fluorescence 90 may be supplied to the third window 77. The fluorescence 90 may pass through the third window 77. The coil 70 and the third window 77 may be aligned in the same direction.

The second sensor 78 may be disposed outside the housing 62 of the third window 77. The second sensor 78 may be disposed adjacent to the first sensor 68. The second sensor 78 may detect the fluorescence 90. The second sensor 78 may include a CMOS or a CCD.

Figure 7:
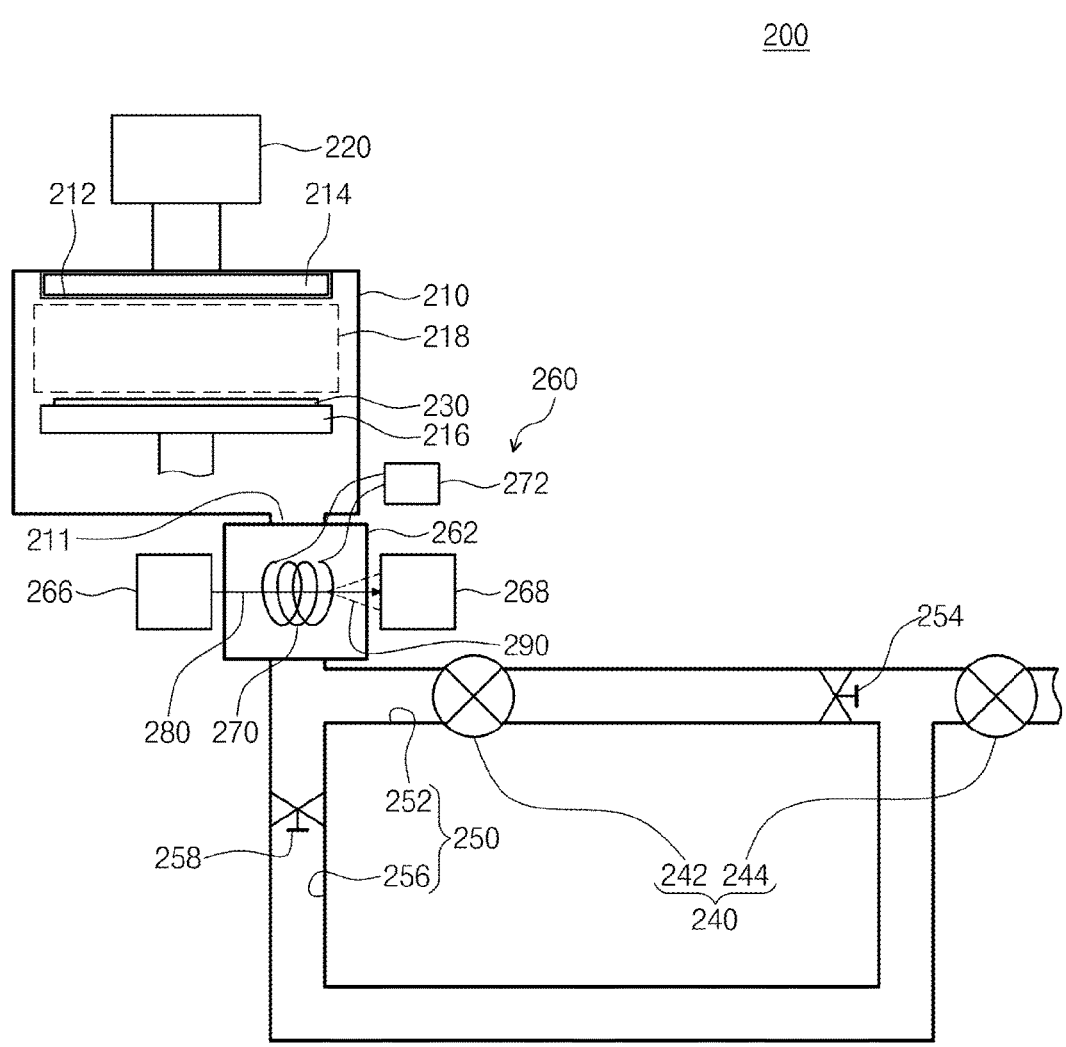
FIG. 7 illustrates plasma process equipment according to another embodiment of the present invention.

FIG. 7 illustrates plasma process equipment 200 according to another embodiment of the present invention. A gas monitoring apparatus 260 may be disposed between a process chamber 210 and a first vacuum pump 242. The gas monitoring apparatus 260 may be connected to an exhaust port 211 of the process chamber 210.

The gas monitoring apparatus 260 and a second vacuum pump 244 may be connected to each other through pumping tubes 250. The first vacuum pump 242 and a main valve 254 may be connected to a main pumping tube 252 between the gas monitoring apparatus 260 and the second vacuum pump 244. A roughing tube 256 may be branched from the main pumping tube 252 between the gas monitoring apparatus 260 and the first vacuum pump 242 and reconnected to main pumping tube 252 between the main valve 254 and the second vacuum pump 244. On the other hand, the first vacuum pump 242 may be disposed between the gas monitoring apparatus 260 and the pumping tubes 250. The first vacuum pump 240 may be connected to the gas monitoring apparatus 260.

Since the process chamber 210, a shower head 212, a chuck 216, a reaction gas supply unit 220, and the gas monitoring apparatus 260 have the same configuration and function as those of the first embodiment, their detailed descriptions will be omitted.

Figure 8:
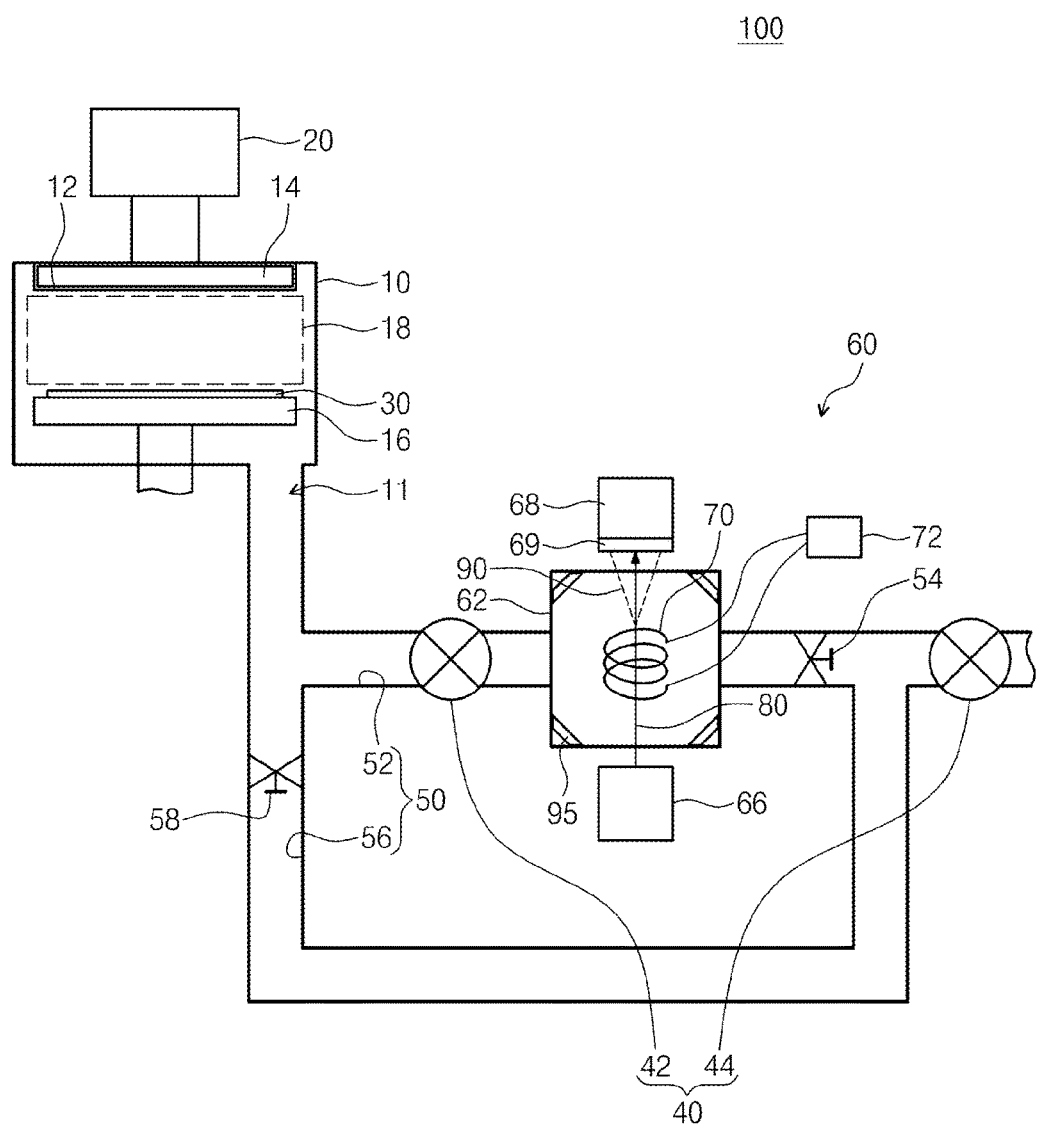
FIG. 8 is a schematic view illustrating plasma process equipment according to a modification of the embodiment of the present invention.

FIG. 8 is a schematic view illustrating plasma process equipment 100 according to a modification of the embodiment of the present invention.

The gas monitoring apparatus 60 may further include reflectors 95 provided in the housing 62. For example, the reflectors 95 may be disposed adjacent to corners in the housing 62. However, the inventive concepts are not limited thereto. The fluorescence 90 generated from activated Si—F species originated from the exhausted product gas by the source light 80 may be emitted in all directions in the housing 62. According to the present embodiment, the reflectors 95 may be controlled by driving apparatus (not shown) such that the fluorescence 90 emitted in the housing 62 is focused on the first sensor 68 (in the embodiment of FIG. 6, the second sensor 78). Thus, the intensity of the fluorescence 90 incident on the first sensor 68 (in the embodiment of FIG. 6, the second sensor 78) can be increased. As a result, the sensing efficiency of the first sensor 68 (in the embodiment of FIG. 6, the second sensor 78) can be improved. Other elements of the plasma process equipment 100 according to the modification of the embodiment of the present invention may be the same as corresponding elements of the plasma process equipment 100 described with reference to FIG. 1.

Even though not shown in the drawings, the reflectors 95 may be applied to the gas monitoring apparatus 60A of FIG. 2, the gas monitoring apparatus 60B of FIG. 5, the gas monitoring apparatus 60C of FIG. 6, and the gas monitoring apparatus 260 of FIG. 7.

As described above, the gas monitoring apparatus according to the embodiments of the present invention may be connected to the pumping tube between the process chamber and the vacuum pumps of the plasma process equipment. The gas monitoring apparatus may detect the fluorescence of the exhausted product gas produced in the cleaning process in the pumping tube without the interference in plasma reaction depositing or etching films.

The description of the present invention is intended to be illustrative, and those with ordinary skill in the technical field of the present invention will be understood that the present invention can be carried out in other specific forms without changing the technical idea or essential features. Therefore, the embodiments described above include exemplary in all respects and not restrictive, but it should be understood.

What is claimed is:
1. An apparatus for monitoring an exhausted product gas exhausted out from a plasma process chamber, the apparatus comprising:
   a housing comprising a gas inflow hole, a gas discharge hole, and windows, the housing being free of plasma reaction therewithin;
   a light source disposed adjacent to one of the windows outside the housing to provide source light to the exhausted product gas supplied between the gas inflow hole and the gas discharge hole, wherein the exhausted product gas flows from the gas inflow hole to the gas discharge hole;
   a sensor disposed adjacent to the other of the windows outside the housing; and
   a heating coil disposed inside the housing between the gas inflow hole and the gas discharge hole, the heating coil being in direct contact with the exhausted product gas flowing from the gas inflow hole to the gas discharge hole,
   wherein the light source generates a blue laser beam or an ultraviolet laser beam as the source light and irradiates the source light to the exhausted product gas, the exhausted product gas irradiated by the source light emits fluorescence having a wavelength longer than that of the source light, and the sensor detects the fluorescence emitted from the exhausted product gas irradiated by the source light,
   wherein the heating coil is a heater which generates heat by an electric power supplied to the heating coil without generating a plasma, and then heats the exhausted product gas between the light source and the sensor, thereby increasing the fluorescence emitted from the exhausted product gas, allowing the fluorescence of the exhausted product gas in the housing to be detected without interference by plasma reaction.

2. The apparatus of claim 1, wherein the heating coil comprises a filament.

3. The apparatus of claim 1, wherein the heating coil proceeds in a direction from the light source to the sensor, while forming a series of loops.

4. The apparatus of claim 1, wherein the exhausted product gas flows in a first direction from the gas inflow hole to the gas discharge hole and the heating coil proceeds in a second direction while forming a series of loops, the second direction crossing the first direction.

5. The apparatus of claim 1, wherein the heating coil is aligned in a direction in which the gas inflow hole and the gas discharge hole are arranged.

6. The apparatus of claim 1, wherein the windows comprises:
   a first window disposed in one sidewall of the housing disposed adjacent to the light source; and
   a second window disposed in the other sidewall of the housing to face the first window,
   wherein the source light passes through the first window and the second window.

7. The apparatus of claim 6, wherein the light source and the sensor are arranged in the same direction as a progressing direction of the source light, and
   the apparatus for monitoring the exhausted product gas further comprising an optical filter for removing the source light between the sensor and the second window.

8. The apparatus of claim 6, wherein the first window and the second window are arranged in a direction in which the gas inflow hole and the gas discharge hole are arranged.

9. The apparatus of claim 1, wherein the windows further comprise a third window disposed in a sidewall of the housing in a diagonal direction with respect to a progressing direction of the source light, and the third window and the heating coil are aligned in the same direction.

10. The plasma process equipment of claim 1, wherein the heating the exhausted product gas includes decomposing the gas.

11. The plasma process equipment of claim 1, further comprising reflectors provided in the housing,
wherein the reflectors are configured to focus the emitted fluorescence on the sensor.

12. The apparatus of claim 1, further comprising a power supply unit which provides the electric power to the heating coil,
wherein the heating coil is heated in proportion to the electric power supplied by the power supply unit.

13. The apparatus of claim 1, wherein the heating coil heats the exhausted product gas at a temperature of about 1000° C. or higher.

14. The apparatus of claim 1, wherein the housing has an inner surface which comes in contact with the exhausted product gas flowing from the gas inflow hole to the gas discharge hole, and the heating coil is disposed inside the housing to be surrounded by and faced by the inner surface.

15. Plasma process equipment comprising:
a plasma process chamber in which a plasma process is performed;
a pumping tube for exhausting an exhausted product gas exhausted out from the plasma chamber; and
a gas monitoring apparatus for detecting an endpoint of the plasma process from the reaction gas in the pumping tube,
wherein the gas monitoring apparatus comprises:
a housing comprising a gas inflow hole, gas discharge hole, and windows, the housing being free of plasma reaction therewithin;
a light source disposed adjacent to one of the windows outside the housing to provide source light to the exhausted product gas supplied between the gas inflow hole and the gas discharge hole, wherein the exhausted product gas flows from the gas inflow hole to the gas discharge hole;
a sensor disposed adjacent to the other of the windows outside the housing; and
a heating coil disposed inside the housing between the gas inflow hole and the gas discharge hole, the heating coil being in direct contact with the exhausted product gas flowing from the gas inflow hole to the gas discharge hole,
wherein the light source generates a blue laser beam or an ultraviolet laser beam as the source light and irradiates the source light to the exhausted product gas, the exhausted product gas irradiated by the source light emits fluorescence having a wavelength longer than that of the source light, and the sensor detects the fluorescence emitted from the gas irradiated by the source light,
wherein the heating coil is a heater which generates heat by an electric power supplied to the heating coil without generating a plasma, and then heats the exhausted product gas between the light source and the sensor, thereby increasing the fluorescence emitted from the exhausted product gas, allowing the fluorescence of the exhausted product gas in the housing to be detected without interference by plasma reaction.

16. The plasma process equipment of claim 15, further comprising a pump connected to the pumping tube,
wherein the pump comprises:
a first pump disposed adjacent to the chamber; and
a second pump connected to the pumping tube disposed on a rear end of the first pump.

17. The plasma process equipment of claim 16, wherein the pumping tube comprises:
a main pumping tube connecting the chamber, the first pump, and the second pump to each other; and
a roughing tube branched from the main pumping tube between the chamber and the first pump, the roughing tube being connected to the main pumping tube between the first pump and the second pump.

18. The plasma process equipment of claim 17, wherein the gas inflow hole and the gas discharge hole are connected to the main pumping tube between the first pump and the second pump.

19. An apparatus for monitoring an exhausted product gas exhausted out from a plasma process chamber, the apparatus comprising:
a housing comprising a gas inflow hole, a gas discharge hole aligned with the gas inflow hole in a first direction, and first and second windows aligned in a second direction crossing the first direction;
a light source disposed adjacent to the first window outside the housing to provide source light in the second direction to the exhausted product gas supplied between the gas inflow hole and the gas discharge hole, wherein the exhausted product gas flows from the gas inflow hole to the gas discharge hole;
a sensor disposed adjacent to the second window outside the housing; and
a heating coil disposed inside the housing between the gas inflow hole and the gas discharge hole, the heating coil being in direct contact with the exhausted product gas flowing from the gas inflow hole to the gas discharge hole,
wherein the light source generates a blue laser beam or an ultraviolet laser beam as the source light and irradiates the source light to the exhausted product gas, the exhausted product gas irradiated by the source light emits fluorescence having a wavelength longer than that of the source light, and the sensor detects the fluorescence emitted from the exhausted product gas irradiated by the source light,
wherein the heating coil is a heater which generates heat by an electric power supplied to the heating coil without generating a plasma, and then heats the exhausted product gas between the light source and the sensor, thereby increasing the fluorescence emitted from the exhausted product gas,
wherein the heating coil has a shape of a helix proceeding in the second direction from the first window to the second window, and the helix forms a series of loops through which the source light from the first window is allowed to passes toward the second window.

* * * * *